US007118536B2

(12) United States Patent
Haberland et al.

(10) Patent No.: US 7,118,536 B2
(45) Date of Patent: Oct. 10, 2006

(54) APNEA/HYPOPNEA DETECTION SYSTEM AND METHOD

(75) Inventors: Ben Haberland, Palm City, FL (US); Uday S Shankar, Murrysville, PA (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 10/895,771

(22) Filed: Jul. 21, 2004

(65) Prior Publication Data

US 2005/0020932 A1 Jan. 27, 2005

Related U.S. Application Data

(60) Provisional application No. 60/490,173, filed on Jul. 25, 2003.

(51) Int. Cl.
*A61B 5/08* (2006.01)
*A61M 16/00* (2006.01)

(52) U.S. Cl. .................. 600/538; 600/529; 128/204.23

(58) Field of Classification Search ........ 600/529–543; 128/204.23, 204.18, 204.21, 204.22

See application file for complete search history.

(56) References Cited

U.S. PATENT DOCUMENTS

| | | | |
|---|---|---|---|
| 5,148,802 | A | 9/1992 | Sanders et al. |
| 5,203,343 | A | 4/1993 | Axe et al. |
| 5,245,995 | A | 9/1993 | Sullivan et al. |
| 5,259,373 | A | 11/1993 | Gruenke et al. |
| 5,295,490 | A | 3/1994 | Dodakian |
| 5,313,937 | A | 5/1994 | Zdrojkowski et al. |
| 5,335,654 | A | 8/1994 | Rapoport et al. |
| 5,433,193 | A | 7/1995 | Sanders et al. |
| 5,458,137 | A | 10/1995 | Axe et al. |
| 5,490,502 | A | 2/1996 | Rapoport et al. |
| 5,535,739 | A | 7/1996 | Rapoport et al. |
| 5,549,106 | A | 8/1996 | Gruenke et al. |
| 5,605,151 | A | 2/1997 | Lynn |
| 5,632,269 | A | 5/1997 | Zdrojkowski et al. |
| 5,645,053 | A | 7/1997 | Remmers et al. |
| 5,685,296 | A | 11/1997 | Zdrojkowski et al. |
| 5,704,345 | A | 1/1998 | Berthon-Jones |
| 5,797,852 | A | 8/1998 | Karakasoglu et al. |
| 5,803,065 | A | 9/1998 | Zdrojkowski et al. |
| 5,803,066 | A | 9/1998 | Rapoport et al. |
| 5,845,636 | A | 12/1998 | Gruenke et al. |
| 5,961,447 | A | 10/1999 | Raviv et al. |
| 6,017,315 | A | 1/2000 | Starr et al. |
| 6,029,664 | A | 2/2000 | Zdrojkowski et al. |
| 6,029,665 | A | 2/2000 | Berthon-Jones |
| 6,085,747 | A | 7/2000 | Axe et al. |

(Continued)

OTHER PUBLICATIONS

U.S. Appl. No. 09/586,054, filed Jun. 2, 2000, Hill et al.

*Primary Examiner*—Charles Marmor
*Assistant Examiner*—Navin Natnithithadha
(74) *Attorney, Agent, or Firm*—Michael W. Haas

(57) ABSTRACT

An apnea/hypopnea detection system and method that monitors a patient's respiratory flow, determines (a) a long term RMS energy based on the flow, (b) a long term threshold determined based on the long term RMS energy, and (c) a short term RMS energy based on the flow. Determining whether the patient is experiencing an apnea/hypopnea is accomplished by comparing the short term RMS energy with the long term threshold. This A/H detection technique is useful in diagnosing a patient for a breathing disorder, such as OSA, and/or for controlling an auto-titration pressure support system.

23 Claims, 4 Drawing Sheets

U.S. PATENT DOCUMENTS

| | | | | |
|---|---|---|---|---|
| 6,138,675 | A | 10/2000 | Berthon-Jones | |
| 6,142,950 | A | 11/2000 | Allen et al. | |
| 6,165,133 | A | 12/2000 | Rapoport et al. | |
| 6,286,508 | B1 | 9/2001 | Remmers et al. | |
| 6,342,040 | B1 | 1/2002 | Starr et al. | |
| 6,360,741 | B1 | 3/2002 | Truschel | |
| 6,367,474 | B1 * | 4/2002 | Berthon-Jones et al. | 128/204.23 |
| 6,368,287 | B1 | 4/2002 | Hadas | |
| 6,502,572 | B1 * | 1/2003 | Berthon-Jones et al. | 128/204.23 |
| 6,544,192 | B1 | 4/2003 | Starr et al. | |
| 6,626,175 | B1 | 9/2003 | Jafari et al. | |
| 6,817,361 | B1 * | 11/2004 | Berthon-Jones et al. | 128/204.18 |

* cited by examiner

APNEA/HYPOPNEA DETECTION SYSTEM AND METHOD

CROSS-REFERENCE TO RELATED APPLICATIONS

This application claims priority under 35 U.S.C. § 119(e) from provisional U.S. patent application No. 60/490,173 filed Jul. 25, 2003 the contents of which are incorporated herein by reference.

BACKGROUND OF THE INVENTION

1. Field of the Invention

The present invention pertains to a system and method for detecting apnea/hypopnea events, and, in particular, to an apnea/hypopnea detection technique based on comparing a root-mean-square (RMS) of a patient's respiratory flow to a target value.

2. Description of the Related Art

Many individuals suffer from disordered breathing during sleep. Sleep apnea is a common example of such disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is defined as a 50% or greater reduction in the peak respiratory air-flow. Other types of disordered breathing include upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

Devices are known that attempt to detect apneas and hypopneas to determine in real time whether a patient suffers from a sleep apnea syndrome. Examples of conventional apnea/hypopnea detection devices are taught in U.S. Pat. No. 5,295,490 to Dodakian; U.S. Pat. No. 5,605,151 to Lynn; U.S. Pat. No. 5,797,852 to Karakasoglu et al.; U.S. Pat. No. 5,961,447 to Raviv et al.; U.S. Pat. No. 6,142,950 to Allen et al.; U.S. Pat. No. 6,165,133 to Rapoport et al.; U.S. Pat. No. 6,368,287 to Hadas.

It is further well known to treat disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's effort, to increase the comfort to the patient. This pressure support technique is referred to a bi-level pressure support, in which the inspiratory positive airway pressure (IPAP) delivered to the patient is higher than the expiratory positive airway pressure (EPAP).

It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing. Thus, the effectiveness of treating a patient via an auto-titration type of pressure support system can depend to a great extent on the accurate detection of apneas and/or hypopneas.

Examples of conventional auto-titration pressure support system are disclosed in U.S. Pat. No. 5,245,995 to Sullivan et al.; U.S. Pat Nos. 5,259,373; 5,549,106, and 5,845,636 all to Gruenke et al.; U.S. Pat. Nos. 5,458,137 and 6,058,747 both to Axe et al.; U.S. Pat. Nos. 5,704,345; 6,029,665, and 6,138,675 all to Berthon-Jones; U.S. Pat. No. 5,645,053 to Remmers et al.; and U.S. Pat. Nos. 5,335,654; 5,490,502, 5,535,739, and 5,803,066 all to Rapoport et al. All of these conventional pressure support systems, with the possible exception of U.S. Pat. No. 5,645,053 to Remmers et al., are reactive to the patient's monitored condition. That is, once a condition occurs that indicates abnormal breathing, the system alters the pressure support to treat this condition.

These conventional A/H detection techniques and auto-titration pressure support systems use a myriad of different techniques to detect apneas and hypopneas. One such technique requires measuring the airflow from the patient and monitoring this airflow to look for reductions during the inspiratory phase indicative of an apnea or hypopnea. This often requires detecting the airflow accurately, which can be difficult in some conditions, for example, if the airflow is being measured via a nasal cannula and the patient is experiencing mouth breathing. Conventional A/H detection techniques also typically require distinguishing between the inspiratory and the expiratory states of the patient in order to focus on the changes in patient flow or pressure occurring during the inspiratory state, which is where the apneas/hypopneas occur. Although techniques exist for distinguishing between the inspiratory and the expiratory states of a patient, this remains a complicated task and is subject to errors.

SUMMARY OF THE INVENTION

Accordingly, it is an object of the present invention to provide an apnea/hypopnea detection system that overcomes the shortcomings of conventional A/H detection techniques. This object is achieved according to one embodiment of the present invention by providing an apnea/hypopnea detection system that includes a flow sensor adapted to detect patient respiratory flow and a processor. The processor calculates the following parameters: (a) a long term RMS energy based on the flow monitored by the flow sensor, (b) a long term threshold determined based on the long term RMS energy, and (c) a short term RMS energy also based on the output of the flow sensor. The processor determines whether a patient is experiencing an apnea/hypopnea event by comparing the short term RMS energy with the long term threshold. By using the RMS energy of the patient's respiratory flow, the present invention avoids the need to distinguish between the inspiratory and expiratory phases of the respiratory cycles, and does not require a highly accurate measurement of the patient's flow in order to provide a relatively accurate A/H detection.

It is yet another object of the present invention to provide an apnea/hypopnea detection method that does not suffer from the disadvantages associated with conventional A/H detection techniques. This object is achieved by providing a method that includes monitoring a patient's respiratory flow; determining a long term RMS energy based on the flow; determining a long term threshold based on the long term RMS energy; determining a short term RMS energy based on the flow; and comparing the short term RMS energy with the long term threshold to determine whether such a patient is experiencing an apnea/hypopnea.

It is a further object of the present invention to employ the A/H detection system and/or method of the present invention in an auto-titration pressure support system to control the pressure delivered to the patient based on whether or not the patient is experiencing apneas/hypopneas.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
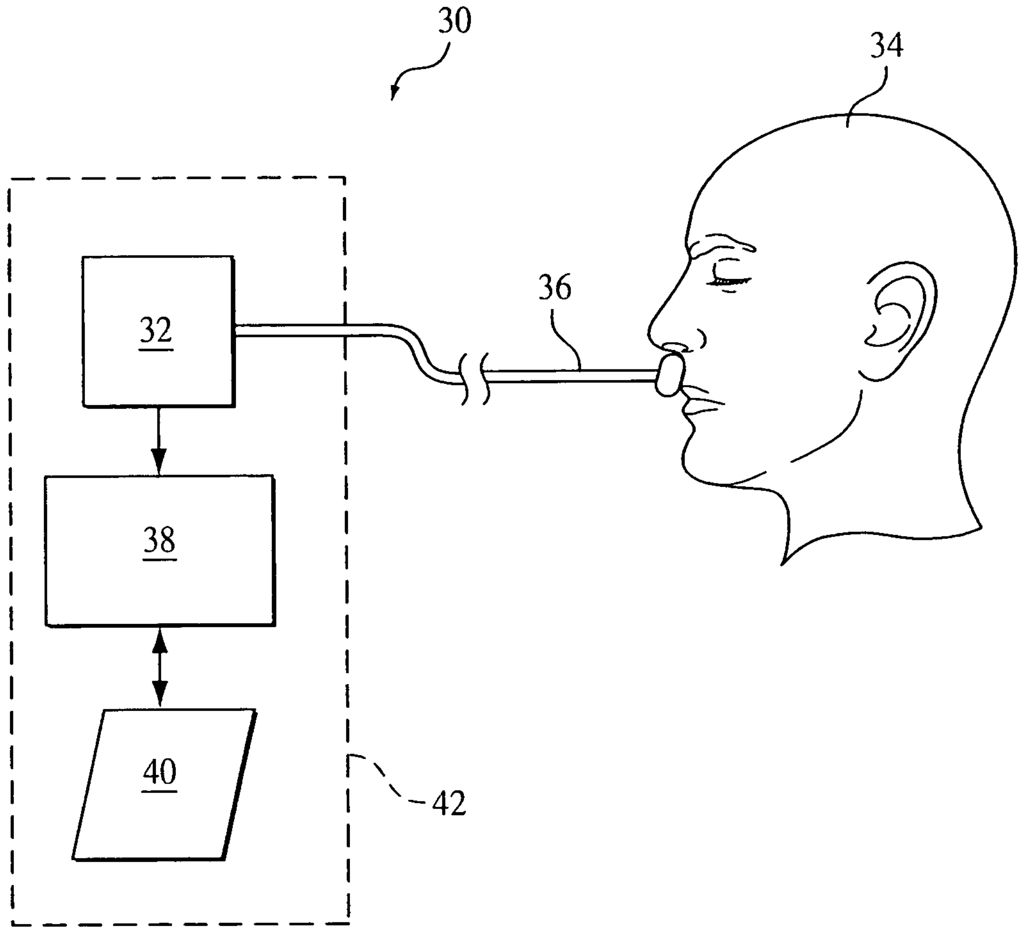
FIG. 1 is a schematic diagram of an apnea/hypopnea detection system according to the principles of the present invention.

FIG. 1 schematically illustrates an exemplary embodiment of an apnea/hypopnea (A/H) detection system 30 according to the principles of the present invention. In its most basic form, detection system includes a sensor 32 in communication with the airway of a patient 34 to measure the flow of gas into and out of the patient, which is referred to as respiratory flow. In the illustrated embodiment, sensor 32 is a conventional flow sensor, such as a differential pressure sensor that communicates with the airway of the patient via a nasal cannula 36.

It is to be understood that the present invention contemplates using any conventional technique for detecting the patient's respiratory flow. For example, the present invention contemplates using the flow sensing technology taught in U.S. Pat. Nos. 6,017,315; 6,342,040; and 6,554,192 all to Starr et al. The present invention also contemplates using a conventional flow sensor, such as a pneumotach, coupled to the patient's airway via a patient interface device, such a nasal or nasal/oral mask.

A/H detection system 30 includes a processor 38, which is preferably a microprocessor capable of implementing a stored algorithm, that receives the output from the flow sensor. Of course, processor 38 includes the necessary memory and processing capability to implement the features of the present invention.

The present invention further contemplates that A/H detection system 30 includes an input/output interface 40 for communicating, information, data and/or instructions and any other communicatable items, collectively referred to as "data", between a user and processor 38. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into processor 38 from the smart card or loaded onto the smart card from the controller. Other exemplary, interface devices and techniques adapted for use with the pressure support system include, but are not limited to, an RS-232 port, CD reader/writer, DVD reader/writer, RF link, and modem (telephone, cable or other). In short, any conventional technique for providing, receiving, or exchanging data with processor 38 are contemplated by the present invention as input/output interface 40.

In the illustrated exemplary embodiment, flow sensor 32, processor 38, and input/output interface 40 are all disposed within single housing, which is schematically illustrated by dashed lines 42 in FIG. 1. It is to be understood, however, that the present invention contemplates that these components can be provided in separate housings. In addition, other components not shown can be added. For example, a bacteria filter may be provided on cannula 36.

The signal from flow sensor 32 is preferably filtered and conditioned. That is, the signal output by sensor 32 is initially sampled by processor 38 at a relatively high frequency, such as 500 Hz. It is then filtered to eliminate bandwith and conditioned by performing anti-aliasing filtering. The resulting output is sampled at a rate of at least twenty (20) samples/second for use in the A/H detection algorithm of the present invention. It should be noted that other sampling rates are contemplated by the present invention. For example, a range of rates from 10 samples/second to 50 samples/second are believed to be suitable for present purposes. This range is believed to be effective in accurately capturing the features of the airway signal of interest.

The A/H detection algorithm is executed by processor 38 and tracks the flow waveform to trigger, indicate, or declare the occurrence of an A/H event at the end of any episode that meets the morphological criteria discussed below. These morphological criteria include the extent of "energy" reduction in the patient flow waveform, the extent of the subsequent "energy" recovery of the waveform, and the duration of the entire episode.

The algorithm executed by processor 38 differs significantly from conventional A/H detection techniques in that it relies strictly on the "energy content" of the air-flow waveform and does not require detecting or classifying individual breaths in terms of their peak amplitudes, I/E times, change in shape, flatness, roundness, or other single breath criteria used in conventional systems. This makes for a very compact and robust algorithm that outperforms the conventional algorithms significantly and one that can be calibrated for a variety of signal acquisition systems.

The A/H detection algorithm is based on the concept that the RMS "energy" of the respiration flow signal can be used to determine apnea and/or hypopnea events being experienced by the patient in real time. Because the overall "energy" of the flow signal is analyzed and not specific breaths or portions of a breath, the present invention has the advantage over conventional A/H detection techniques in that it does rely on breath detection as part of the A/H detection scheme.

Figure 2:
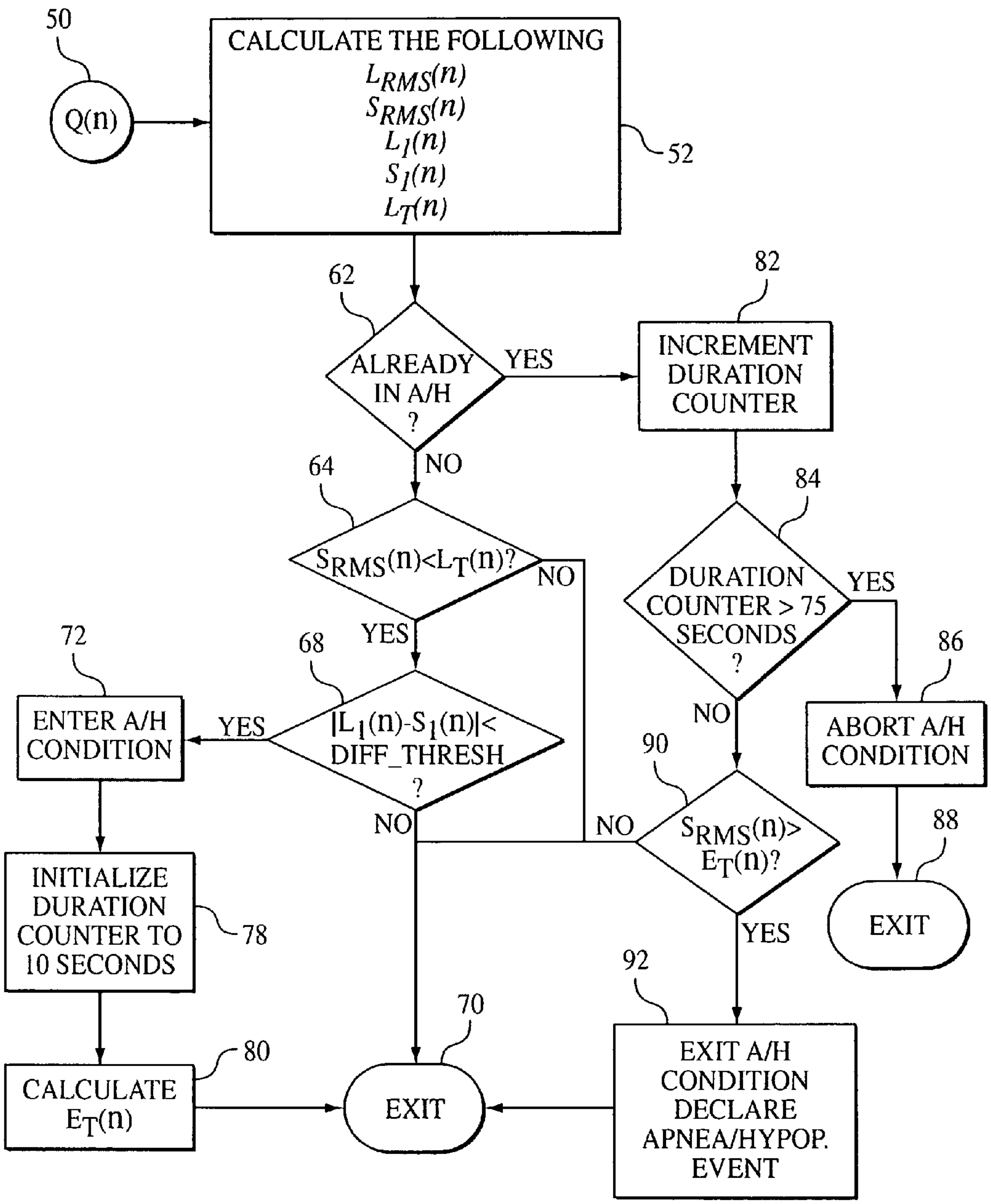
FIG. 2 is a flowchart illustrating the A/H detection technique of the present invention.
Figures 3A, 3B, 3C:
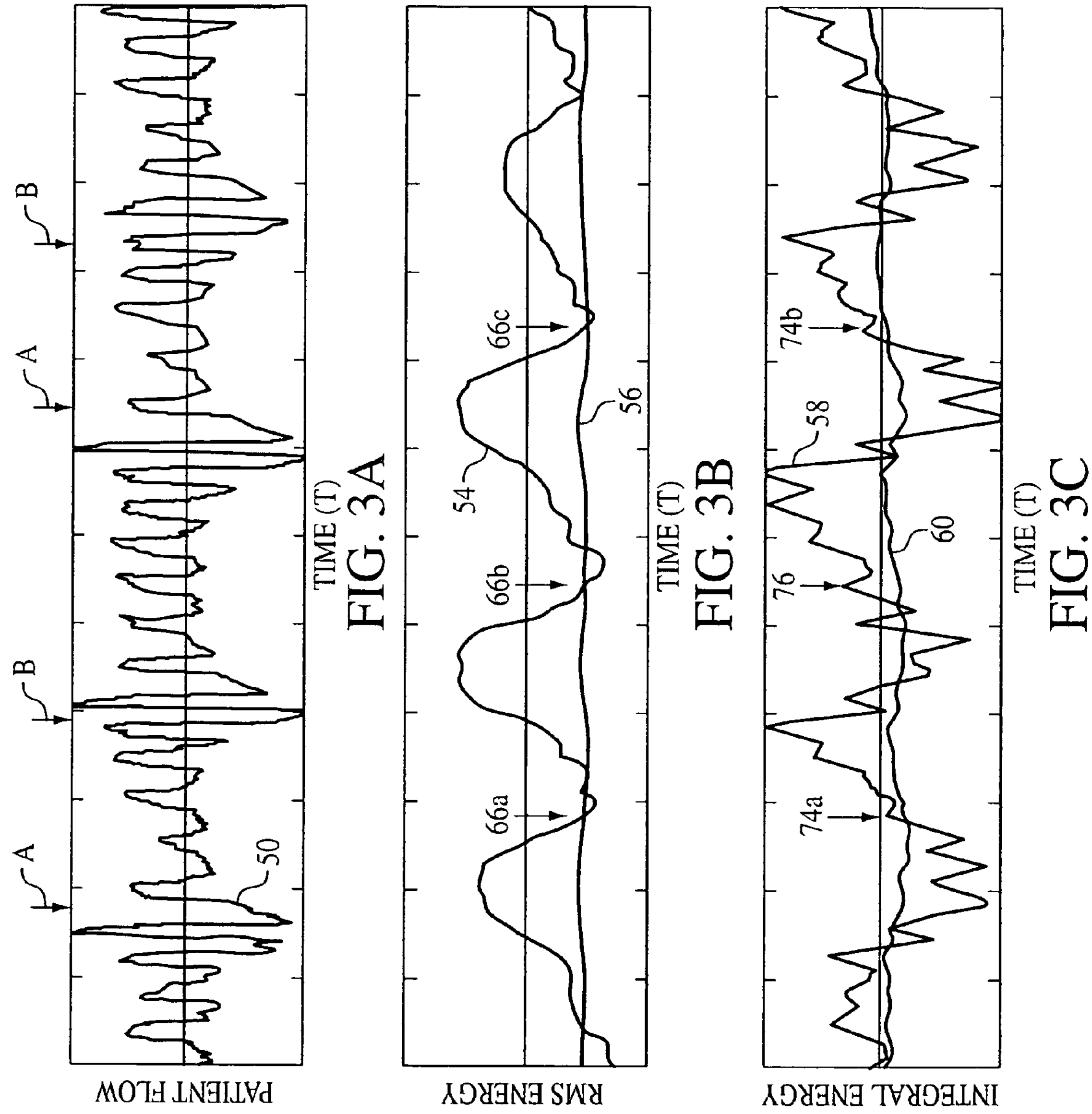
FIGS. 3A–3C are waveforms illustrating the processing carried out by the flowchart of FIG. 2.

Referring now to FIGS. 2–3C, the A/H detection technique of the present invention will be discussed. FIG. 2 is a flow chart illustrating the overall operation of the A/H detection algorithm, and FIGS. 3A–3C illustrate exemplary waveforms produced at various steps implemented during execution of the algorithm. The input signal to the A/H detection algorithm is the patient respiratory flow signal 50 sampled at the sampling rate "f", which, as noted above, is preferably 20 Hz in the current implementation. An example of respiratory flow signal 50 is shown in FIG. 3A and is provided as the input to step 52 in the FIG. 2. The respiratory flow signal 50 during a current processing cycle "n" is represented as Q(n). The A/H detection algorithm of FIG. 2 is executed f times a second, where f is the sampling frequency, e.g., 20 Hz. Each time the A/H detection algorithm is executed, a respiratory flow signal Q(n) is provided as input to step 52.

In step 52, which is entered during every pass through the algorithm, i.e., every 1/f of a second, the following five parameters are computed: a short term RMS energy $S_{RMS}$(n) (waveform 54 FIG. 3B); a long term RMS energy $L_{RMS}$(n); short term integral of the patient flow $S_I$(n) (waveform 58 FIG. 3C); a long term integral of the patient flow $L_I$(n) (waveform 60 FIG. 3C); and a long term threshold $L_T$(n) (waveform 56 FIG. 3B). Each of these parameters is discussed in detail below.

The short term RMS energy $S_{RMS}$(n) waveform 54 is the root-mean-square (RMS) of respiratory flow signal 50 over the last $T_S$ seconds is computed. The short term RMS energy is calculates as follows:

$$S_{RMS}(n)=\sqrt{\frac{1}{N_S}*\sum_{k=0}^{N_S-1}[Q(n-k)]^2}, \quad (1)$$

where, $N_S=T_S$*f, $T_S$ is the length of time in seconds over which short term RMS energy is calculated, and f is the sampling frequency. It can be appreciated that $N_S$ represents the number of samples over the period of time of interest, namely period $T_S$.

In an exemplary embodiment of the present invention, $T_S$ is set at 10 seconds, because 10 seconds is the clinically recognized minimum duration of time that must pass before an apnea/hypopnea condition will be declared. That is, any detectable perturbation in this short term RMS energy must encompass the previous 10 seconds in order for that perturbation to be considered an apnea/hypopnea.

It is to be understood that the present invention is not limited to a duration of 10 second for $T_S$. However, greater durations for $T_S$ could result in failing to detect flow limitations that would otherwise be declared an apnea/hypopnea. Conversely, shorter durations could result in the algorithm detect flow limitations that should not be declared an apnea/hypopnea.

Waveform 54 in FIG. 3B illustrates the short term RMS energy $S_{RMS}$(n) waveform based on waveform 50 of FIG. 3A. In can be appreciated from reviewing waveform 54 with respect to patient respiratory flow 50 in FIG. 3A, that as the patient begins to experience and apnea or hypopnea, which begins, for example, at the locations indicated by arrows A in FIG. 3A, the short term RMS energy $S_{RMS}$(n) waveform begins to fall. This is so because there is less RMS energy in the patient's respiratory waveform the longer they continue into the apnea episode. Conversely, as the patient begins to recover from the apnea or hypopnea episodes the short term RMS energy $S_{RMS}$(N) waveform increases.

The long term RMS energy $L_{RMS}$(n) is the root-mean-square of respiratory flow signal 50 computed over the last $T_L$ seconds. The long term RMS energy is calculates as follows:

$$L_{RMS}(n)=\sqrt{\frac{1}{N_L}*\sum_{k=0}^{N_L-1}[Q(n-k)]^2}, \quad (2)$$

where $N_L=T_L$*f, $T_L$ is the length of time in seconds over which long term RMS energy is calculated, and f is the sampling frequency. It can be appreciated that $N_L$ represents the number of samples over the period of time of interest, namely period $T_S$. It should be noted that the long term RMS energy $L_{RMS}$(n) is not illustrated in FIGS. 3A–3C.

In an exemplary embodiment of the present invention, $T_L$ is chosen to be 95 seconds. A duration of 95 seconds was selected from empirical studies of patient data encompassing different breath rates, breathing types, breath amplitudes, and breathing disorders. It is to be understood that the present invention is not limited to a duration of 95 second for $T_L$. A range of values can be chosen for $T_L$ based on the typical epoch lengths used by sleep technicians to view airflow data. Based on these "views", sleep technicians visually estimate "long term" or "baseline" values of peak flow. The typical epoch lengths are 1 to 2 minutes. Any duration greater than this range becomes physiologically irrelevant in A/H detection. Anything shorter is inadequate to make a determination of "baseline".

The long term RMS energy $L_{RMS}$(n) is used to calculate a long term threshold $L_T$(n) as follows:

$$L_T(n)=L_{RMS}(n)\times(\text{entry threshold fraction}), \quad (3)$$

where the entry threshold fraction is another empirically derived constant. In an exemplary embodiment of the present invention, the entry threshold fraction is set to be 0.56, so that the long term threshold $L_T(n)$=56% of $L_{RMS}(n)$. Waveform 56 in FIG. 3B illustrates the long term threshold $L_T(n)$. As can be seen in FIG. 3B, the long term threshold $L_T(n)$ rises and falls in much the same manner as the short term RMS energy $S_{RMS}(n)$, except on a much smaller scale.

It is to be understood that the present invention is not limited to a specific value for the entry threshold fraction. The RMS energy is direction proportional to the peak flow. Therefore, going by the definition of hypopnea (50% reduction in peak flow), and given empirical trials, the "entry threshold fraction" should be in the range of 50% of the long term RMS energy $L_{RMS}(n)$,±10%.

The short term integral $S_I(n)$ of patient flow 50 determined in step 52 is of the summation of the respiratory flow signal over the last $T_S$ seconds. It is calculated as follows:

$$S_I(n) = \sum_{k=0}^{N_S-1} Q(n-k), \tag{4}$$

Waveform 58 in FIG. 3C illustrates the short term integral $S_I(n)$. It can be appreciated from reviewing FIG. 3C that the short term integral decreases as the patient begins to experience and apnea/hypopnea and increases as he or she recovers from the apnea/hypopnea.

The long term integral $L_I(n)$ of patient flow 50 is the summation of the respiratory flow signal over the last $T_S$ seconds and is calculated as follows:

$$L_I(n) = \sum_{k=0}^{N_L-1} Q(n-k), \tag{5}$$

Waveform 60 in FIG. 3C illustrates the long term integral $L_I(n)$. As can be seen in FIG. 3C, the long term integral $L_I(n)$ rises and falls in much the same manner as the short term integral, except on a much smaller scale.

Having calculated these parameters (updated for the current processing cycle (n)), in step 62, the algorithm determines whether the patient is currently in an apnea/hypopnea conditions, which is explained more fully below. If the patient is not currently in the A/H condition, i.e., the patient is not deemed to be currently experiencing an apnea/hypopnea, the algorithm proceeds to step 64 where the determination of whether the patient is experiencing an apnea/hypopnea begins.

In step 64, the short term RMS energy $S_{RMS}(n)$ is compared to the long term threshold $L_T(n)$. More specifically, if short term RMS energy $S_{RMS}(n)$ 54 falls below long term threshold $L_T(n)$ 56, which occurs in FIG. 3B at points 66*a*, 66*b*, and 66*c*, the algorithm moves to step 68. If short term RMS energy 54 is above long term threshold $L_T(n)$ 56, the routine ends at step 70 and returns to step 52, where it begins again at the next processing cycle.

In step 68, the absolute difference between long term integral $L_I(n)$ 60 and short term integral $S_I(n)$ 56 is compared to a difference threshold (which is indicated as "diff_thresh" in FIG. 2). If the absolute difference between long term integral $L_I(n)$ 60 and short term integral $S_I(n)$ 56 is less than this threshold, which occurs at points 74*a* and 74*b* in FIG. 3C, an apnea/hypopnea condition is entered in step 72. If the absolute difference between long term integral 60 and short term integral 56 is not less than this threshold, which occurs at points 76 in FIG. 3C, the routine ends at step 70 and returns to step 52, where it begins again at the next processing cycle. Thus, the A/H detection technique of the present invention only considers the patient to have entered an A/H condition if both (1) short term RMS energy $S_{RMS}(n)$ 54 falls below long term threshold $L_T(n)$ 56 (step 64) and (2) the absolute difference between long term integral $L_I(n)$ 60 and short term integral $S_I(n)$ 56 is less than the difference threshold (step 68).

The difference threshold is an empirically determined threshold. By requiring this comparison in step 68, the algorithm of the present invention prevents spurious apnea/hypopnea detections that may otherwise result from abrupt changes the sensed patient flow, which can occur if there is a sharp change in the leak of gas from the system in an auto-titration pressure support system or if the entire flow signal gets swamped by patient movement.

It can be appreciated that the difference threshold is an exclusionary criteria. If the system/signal is stable, the expectation is that the excursion of the short term integral $S_I(n)$ from the long term integral $L_I(n)$ will not be too great in either direction. For example, given a sampling rate of 20 samples/second, $T_L$=95 seconds, $T_S$=10 seconds, and assuming a pure sinusoidal air flow waveform with a period of 5 seconds, the short term integral $S_I(n)$ is an extremely small sinusoidal perturbation, while the long term integral $L_I(n)$ is an almost steady DC signal with an even smaller sinusoidal perturbation. In this stable situation, the absolute difference $|S_I(n)-L_I(n)|$ depends on the amplitude of the original sinusoid. Regardless of what the amplitude may be, and because the overall signal/system is stable, there will be no actual "exclusionary" step. However, when there is a large artifact, for example, due to movement or leak, the behavior of the absolute difference $|S_I(n)-L_I(n)|$ is more complex and it assumes much larger values. Thus, the choice of the difference threshold should be such that it is large enough to accommodate "normal" values for the absolute difference $|S_I(n)-L_I(n)|$ associated with stable signals across a range of amplitudes. On the other hand, the difference threshold should be set small enough to track the larger excursions associated with artifacts, such as movement, leak, etc, effectively.

The present inventors also noted that the short and long term integrals $S_I(n)$, $L_I(n)$ have a different phasic relationship with respect to the short term and long term RMS energies $S_{RMS}(n)$, $L_{RMS}(n)$. That is, the response of the short and long term integrals is faster than the that of the short and long term RMS energies. Therefore, for best tracking of the maximal perturbation in the absolute difference $|S_I(n)-L_I(n)|$ due to artifacts, such as movement, leak, etc., the present invention takes into consideration the behavior of the absolute difference $|S_I(n)-L_I(n)|$ sometime prior to the instant n when the decision is made to declare an A/H condition (based on the RMS energy criteria described earlier). The period of time prior to the instant n when the decision is made to declare an A/H condition is another empirically determined constant "difference lag" or DL. In which case, the following relation is used in step 68: $|S_I(n-DL)-L_I(n-DL)|$.

In an exemplary embodiment of the present invention, the choice of difference threshold was empirically determined from studies with different patient breath amplitudes under normal conditions and subject to abrupt artifacts and determined to be 3.1 LPM. This would vary considerably in other systems without an absolute measure of the air flow, such as nasal cannulas. The choice of DL was also made based on the same patient data set and chosen to be 23 samples, i.e., a little over 1 second. Again, this would vary for systems with different transfer functions at any stage from the patient's air flow to the filtered and conditioned air flow "waveform".

When an A/H condition is entered in step 72, the patient is already 10 seconds into the apnea/hypopnea condition due to $T_S$ being set to 10 seconds. Therefore, an apnea/hypopnea duration counter is initialized in step 78 to 10 seconds. The apnea/hypopnea duration counter is incremented every second from this point until the A/H condition ceases or the algorithm otherwise terminates.

In step 80, an exit threshold $E_T(n)$ is calculated based on the long term threshold $L_T(n)$. More specifically, the exit threshold is calculated as follows:

$$E_T(n)=L_T(n)\times(\text{exit\_threshold\_fraction}), \quad (6)$$

where the exit_threshold_fraction is yet another empirically derived constant. The purpose of the exit threshold is to effectively track the recovery of a patient from an A/H condition. That is, before the apnea/hypopnea condition is deemed to end, short term RMS energy $S_{RMS}(n)$ 54 must rise above long term threshold 56 by a sufficient amount.

Recovery from an A/H condition, especially an obstructive A/H condition is marked by a sharp intake of breath and a complete or partial return to the baseline amplitudes for peak flow. Therefore, the criteria for exiting an A/H condition involves the calculation of an exit threshold one time upon entry into the A/H condition. The exit threshold is preferably set to 70%–100% of the baseline $L_{RMS}(n)$ at the start of the A/H condition. In the present implementation, the exit threshold is chosen to be about two times the entry threshold (which is itself about 50% of baseline). After the exit threshold is calculated in step 80, the algorithm returns to step 52 via exit step 70.

The next time the algorithm is executed, i.e., during the next processing cycle, the parameters $S_{RMS}(n)$, $L_{RMS}(n)$, $S_I(n)$, $L_I(n)$, and $L_T(n)$ are recalculated for that processing cycle. It can be appreciated, however, that only the short term RMS energy $S_{RMS}(n)$ need be recalculated as this is the only variable that is acted upon if the patient is already deemed to be in an apnea/hypopnea condition. Thus, if the patient is deemed to be in an A/H condition, the parameters $L_{RMS}(n)$, $S_I(n)$, $L_I(n)$, and $L_T(n)$ need not be recalculated.

In step 62, the algorithms determines whether the patient is currently in an apnea/hypopnea conditions, i.e., whether an A/H condition was entered by entering step 72. If the patient is currently in an apnea/hypopnea condition, the duration counter is incremented in step 82. Incrementing the duration counter can be done every processing cycle based on the processing speed or the duration counter can be a timer that is allowed to run.

In step 84, the algorithm determines whether the patient has been in the apnea/hypopnea condition for greater than 75 seconds based on the amount of time accumulated on the duration counter. It has been clinically determined that a human cannot remain in an apnea/hypopnea condition for more than 75 seconds. Therefore, the algorithm considers the A/H condition to have been erroneously entered if the duration counter exceeds 75 seconds and terminates the algorithm in step 86 and exits in step 88. At which time, the duration counter is reset and the process returns to step 52.

If the duration counter is not greater than 75 seconds, the process continues to step 90 where the short term RMS energy $S_{RMS}(n)$ is compared to the exit threshold $E_T(n)$. If the short term RMS energy $S_{RMS}(n)$ is not greater than the exit threshold $E_T(n)$ during this pass through the algorithm, which will be the case during the middle of the A/H episode, the process exits at step 70 and returns to the beginning at step 52. If, however, the short term RMS energy $S_{RMS}(n)$ is greater than the exit threshold $E_T(n)$ in step 90, which eventually happens as the patient recovers from the A/H episode, the process proceeds to step 92 and the determination is made that the patient has exited or ended the A/H condition. Arrows B in FIG. 3A illustrates the locations where the short term RMS energy $S_{RMS}(n)$ has exceeded the exit threshold $E_T(n)$ so that the A/H condition is deemed to have ended. It can thus be appreciated that the algorithm of the present invention detects the onset of the A/H condition, monitors the patient throughout the A/H episode, and determines that the patient has ended the A/H condition.

The determination that the patient has experienced and A/H episode can be used in any conventional fashion. For example, a simple patient monitor may count the number of times the patient experiences an apnea/hypopnea over a given period of time to determine the patient's apnea/hypopnea index, which is a clinically recognized criteria for diagnosing a patient as suffering from sleep apnea. When implemented in an auto-titration pressure support system, the output of the A/H detection algorithm may be used to adjust the pressure being provided to the patient.

Figure 4:
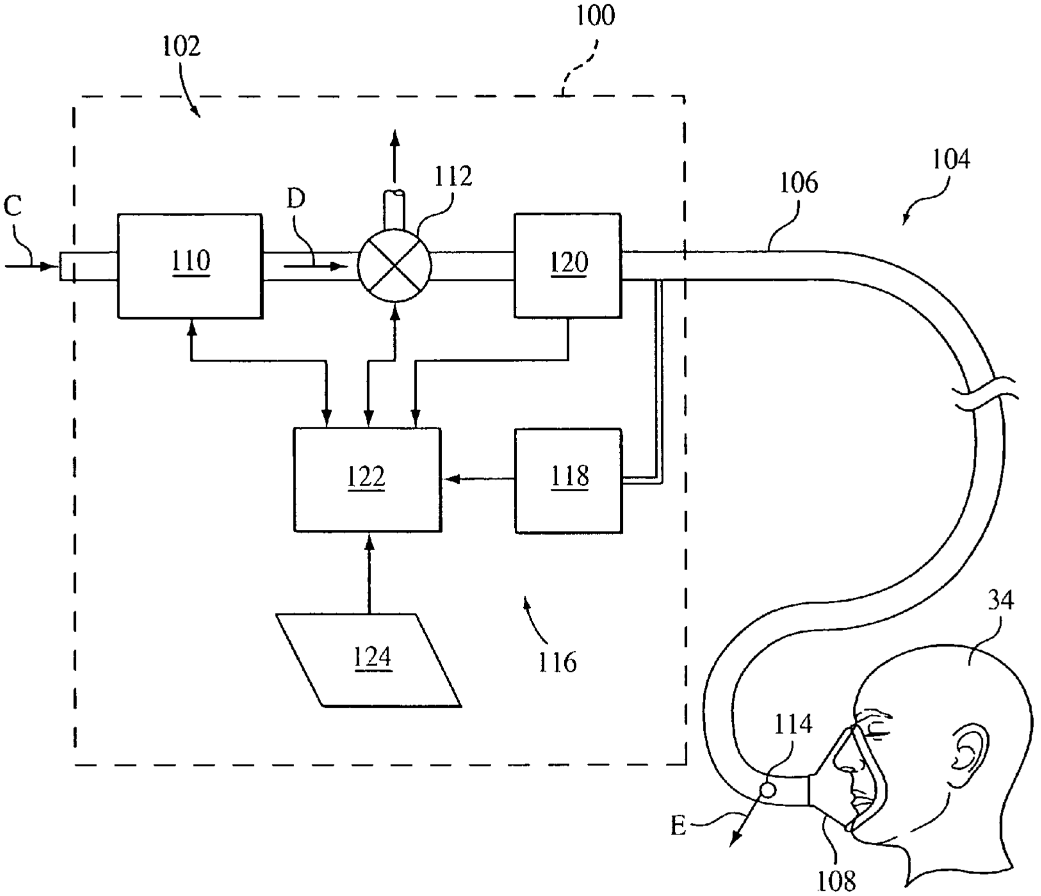
FIG. 4 is a schematic diagram of an auto-titration pressure support system incorporating the apnea/hypopnea detection system of the present invention.

FIG. 4 schematically illustrates an example of an auto-titration pressure support system 100 that includes the above-described A/H detection technique of the present invention. Pressure support system 100 includes a pressure generating system, generally indicated at 102, and a patient circuit 104, which includes a conduit 106 and a patient interface device 108. In the illustrated embodiment, pressure generating system 102 includes a pressure generator 110 and a pressure control valve 112 as the outlet of the pressure generator.

Pressure generator 110 receives the breathing gas from a source of breathing gas, as indicated by arrow C, and outputs the breathing gas, as indicated by arrow D, to patient circuit 104 at a pressure that is greater than atmosphere for delivery to the airway of a patient (not shown). Pressure generator 110 is a mechanical pressure generator, such as a blower, bellows, or piston, that receives ambient air, for example, at an inlet from the gas source. Pressure control valve 112 controls the pressure of the flow of breathing gas delivered to the patient via the patient circuit by restricting the flow to the patient, by diverting flow from patient circuit 104, as indicated by arrow D, or a combination thereof.

The pressure of the flow of breathing gas delivered to the patient is regulated by controlling the operating speed of pressure generator 110, either alone or in combination with valve 112. Of course, valve 112 can be eliminated if operating speed alone is used to control the pressure of the flow of breathing gas delivered to the patient. Those skilled in the art can appreciate that other techniques for controlling the pressure of the flow of breathing gas delivered to the patient can be implemented in pressure support system 100, either alone or in combination to those discussed above. For example, a flow restricting valve (not shown) can be provided upstream of pressure generator 110 that controls the flow (arrow C) of gas to pressure generator 110, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as valve 112, would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 4, the present invention also contemplates providing a secondary flow of gas, either alone or in combination with the primary flow of gas (arrow C) from atmosphere. For example, a flow of oxygen from any suitable source can be provided upstream to pressure generator 110 or downstream of the pressure generator in the patient circuit or at the patient interface device to control the fraction of inspired oxygen delivered to the patient.

In the illustrated embodiment, conduit 106 in patient circuit 104 has one end coupled to the output of the pressure generator 110 and another end coupled to patient interface device 108. Conduit 106 is any tubing capable of carrying the gas flow from the pressure generator to the airway of the patient. Typically, a distal portion of the conduit 106 relative to pressure generator 110 is flexible to allow for freedom of movement of the patient. It is to be understood that various components may be provided in or coupled to patient circuit 104. For example, a bacteria filter, pressure control valve, flow control valve, sensor, meter, pressure filter, humidifier and/or heater can be provided in or attached to the patient circuit. Likewise, other components, such as muffler and filters can be provided at the inlet of pressure generator 110 and at the outlet of valve 112.

Patient interface device 108 is any device suitable for communicating an end of conduit 106 with the airway of the patient. Examples of suitable patient interface devices include a nasal mask, oral mask or mouthpiece, nasal/oral mask, nasal cannula, trachea tube, intubation tube, hood, or full face mask. It is to be understood that this list of suitable interface devices is not intended to be exclusive or exhaustive.

In the illustrated single limb patient circuit, exhaled gas from the patient typically exits the patient circuit via an exhaust vent 114, as indicated by arrow E, provided on a distal portion of conduit 104. Typically, exhaust vent 114 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

FIG. 4, pressure support system 100 includes a monitoring system, generally indicated at 116, to monitor the flow and pressure of gas delivered to the patient. In the illustrated embodiment, monitoring system 116 includes a flow sensor 118 that measures a rate at which the breathing gas flows within patient circuit 104. Flow sensor 118 is functionally equivalent to flow sensor 32 discussed above. The present invention contemplates that any suitable sensor, such as a conventional pneumatach, can be used for flow sensor 118.

It is to be further understood that flow sensor 118 need not be coupled directly to conduit 106. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 110. In short, the present invention contemplates any conventional technique for measuring the flow of gas delivered to the patient.

Monitoring system 116 also includes a pressure sensor 120 that detects the pressure of the gas at the patient. In the illustrated embodiment, pressure sensor 120 is in fluid communication with patient interface device 108 via a conduit 106. In this embodiment, the pressure at the patient is estimated based on the known pressure drop that occurs in tubing 106. It is to be understood, however, that the patient pressure can be measured directly at patient interface device 108.

Pressure support system 100 includes a controller 122, which is preferably a microprocessor capable of implementing a stored algorithm, that receives the monitored variables, typically from flow sensor 118 and pressure sensor 120, and controls pressure generating system 102 based on these signals. Of course, controller 122 includes the necessary memory and processing capability to implement the features of the present invention. Controller 122 is functionally equivalent to processor 38 discussed above.

Pressure support system 30 includes an input/output interface 124 for communicating, information, data, and/or instructions and any other communicatable items, collectively referred to as "data", between a user and controller 122. Input/output interface 124 is functionally equivalent to input/output interface 40 discussed above. Therefore, no further details need be provided regarding interface 124.

Controller 122 performs the A/H detection technique of the present invention, as well as any other functions needed to implement an auto-titration pressure support, such as conventional leak estimation and respiratory cycle monitoring techniques. In this manner, flow sensor 118 and controller 122 provide the basic components of A/H detection system 30 discussed above. The output of the A/H determination, i.e., whether or not the patient is experiencing an apnea/hypopnea, is used by controller 122 to control the pressure provided to the patient in any conventional manner. For example, if a certain number of apneas are detected over a certain period of time, the pressure provided to the patient can be increased by the controller by a given amount to treat the condition. Conversely, if few or no apneas are detected over a certain period of time, the pressure provided to the patient can be decreased by the controller to minimize the pressure being provided to the patient.

The present invention contemplates using any conventional technique for calculating leak $Q_{leak}$, which is the leakage of gas from the pressure support system and includes intentional leaks from the exhaust vent (arrow E) and unintentional leaks from the mask-patient interface, for example. The present invention also contemplates using any conventional technique for taking leak into consideration when determining the patient flow $Q_{patient}$, which is the flow of gas at the airway of the patient and which corresponds to Q(n) input to the A/H detection algorithm, and total flow $Q_{total}$, which is the flow of gas typically measured by flow sensor 46. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,360,741 to Truschel, and pending U.S. patent application Ser. No. 09/586,054 to Frank et al. and Ser. No. 09/970,383 to Jafari et al., the contents of each of which are incorporated by reference into the present invention, all teach techniques for detecting and estimating leak and managing the delivery of breathing gas to the patient in the presence of leaks.

Although not necessary for implementing the A/H detection technique of the present invention, any conventional technique for detecting the inspiratory and expiratory phases of the patient's respiratory cycle can also be carried out by controller 122. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., and pending U.S. patent application No. 09/970,383 to Jafari et al., all teach techniques for differentiating between the inspiratory and expiratory phases of a respiratory cycle. Detecting the inspiratory and expiratory phases of the patient's respiratory cycle may be necessary for implementing certain aspects of the auto-titration pressure support technique other than the A/H detection technique of the present invention.

In the above embodiment of the present invention, the determination of parameters used in the A/H detection algorithm ($S_{RMS}$(n), $L_{RMS}$(n), $S_I$(n), $L_I$(n), $L_T$(n), and $E_T$(n)) were expressed in terms of the discrete-time domain, i.e., based on the sampling number (n). Those skilled in the art will understand that these parameters can also be expressed in the continuous-time domain ($S_{RMS}$(t), $L_{RMS}$(t), $S_I$(t), $L_I$(t), $L_T$(t), and $E_T$(t)). The following equations (7)–(12) show the continuous-time domain equivalent to equations (1)–(6), respectively:

$$S_{RMS}(t) = \sqrt{\frac{1}{T_S} * \int_{t-T_S}^{t} [Q(\tau)]^2 \, d\tau}\,, \tag{7}$$

$$L_{RMS}(t) = \sqrt{\frac{1}{T_L} * \int_{t-T_L}^{t} [Q(\tau)]^2 \, d\tau}\,, \tag{8}$$

$$L_T(t) = L_{RMS}(t) \times (\text{entry threshold fraction}), \tag{9}$$

$$S_I(t) = \int_{t-T_S}^{t} Q(\tau) d\tau, \tag{10}$$

$$L_I(t) = \int_{t-T_L}^{t} Q(\tau) d\tau, \text{ and} \tag{11}$$

$$E_T(t) = L_T(t) \times (\text{exit\_threshold\_fraction}). \tag{12}$$

In the embodiment illustrated in FIG. 4, the A/H detection system and the treatment system, i.e., the pressure support system, are physically combined in one housing, which is also the case in any conventional auto-titration system. However, the present invention also contemplates that the A/H detection system can be physically separated from the patient treatment system. For example, the A/H system can be provided as a modular component that is capable of pigging-backing on top of a conventional pressure support system that is otherwise not auto-titrating. In this embodiment, the input to the A/H detection system, i.e., patent flow, is either taken from the host pressure support system, if this capability exists, or monitored independently, for example, by providing a flow sensor in a patient circuit. The output of the A/H detection system is provided to the pressure control system in the host system, which uses this information to adjust the pressure delivered to the patient. Thus, a relatively inexpensive conventional CPAP system, can be turned into a relatively sophisticated auto-titration pressure support using the modular A/H detection component.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An apnea/hypopnea detection system comprising:

a flow sensor adapted to detect patient respiratory flow; and processing means for: (1) determining (a) a long term RMS energy based on the flow, (b) a long term threshold determined based on the long term RMS energy, and (c) a short term RMS energy based on the flow, (2) determining whether a patient is experiencing an apnea/hypopnea event by comparing the short term RMS energy with the long term threshold, (3) calculating (a) a short term integral of the patient flow, (b) a long term integral of the patient flow, and (c) an absolute difference therebetween, and (4) determining whether a patient is experiencing an apnea/hypopnea event that includes comparing the absolute difference to a differential threshold.

2. The system of claim 1, wherein determining the long term threshold includes multiplying the long term RMS energy by an entry threshold fraction.

3. The system of claim 1, wherein determining whether a patient is experiencing an apnea/hypopnea event includes determining whether the short term RMS energy falls below the long term threshold.

4. The system of claim 1, wherein the differential threshold is an empirically determined value.

5. The system of claim 1, wherein the processing means the short term RMS energy, $S_{RMS}$(n), as:

$$S_{RMS}(n) = \sqrt{\frac{1}{N_S} * \sum_{k=0}^{N_S-1} [Q(n-k)]^2}\,,$$

where $N_S$=$T_S$–f, Q(n) is the patient flow, n is processing cycle, f is the sampling frequency, and $T_S$ is a period of time over which the short term RMS values is calculated.

6. The system of claim 1, wherein the processing means the long term RMS energy $L_{RMS}$(n) as:

$$L_{RMS}(n) = \sqrt{\frac{1}{N_L} * \sum_{k=0}^{N_L-1} [Q(n-k)]^2}$$

where $N_L$=$T_S$–f, Q(n) is the patient flow, n is processing cycle, f is the sampling frequency, and $T_L$ is a period of time over which the long term RMS values is calculated.

7. The system of claim 1, wherein the long term integral energy $L_I(n)$ is determined as:

$$L_I(n) = \sum_{k=0}^{N_L-1} Q(n-k)$$

where $N_L=T_S-f$, Q(n) is the patient flow, n is processing cycle, f is the sampling frequency, and $T_L$ is a period of time over which the long term RMS values is calculated.

8. The system of claim 1, wherein the short term integral energy $S_I(n)$ is determined as:

$$S_I(n) = \sum_{k=0}^{N_S-1} Q(n-k)$$

where $N_S=T_S-f$, Q(n) is the patient flow, n is processing cycle, f is the sampling frequency, and $T_S$ is a period of time over which the short term RMS values is calculated.

9. The system of claim 1, further comprising a conduit coupled to an airway of such a patient, and wherein the flow sensor is coupled to the conduit.

10. The system of claim 1, further comprising a pressure generating system adapted to generate a flow of gas, and wherein the processing means controls a pressure of a flow of gas output of the pressure generating system based on whether such a patient is experiencing the apnea/hypopnea event.

11. An apnea/hypopnea detection system comprising:

a flow sensor adapted to detect patient respiratory flow; and processing means for (1) determining (a) a long term RMS energy based on the flow, (b) a long term threshold determined based on the long term RMS energy, and (c) a short term RMS energy based on the flow, (2) determining whether a patient is experiencing an apnea/hypopnea event by comparing the short term RMS energy with the long term threshold, and (3) determining whether such a patient has ceased experiencing an apnea/hypopnea event that includes calculating an exit threshold that is different from the long term threshold, and comparing the short term RMS energy with the exit threshold.

12. The system of claim 11, wherein the processing means determines the exit threshold based on the long term threshold.

13. A method of detecting an apnea/hypopnea comprising:

monitoring a patient's respiratory flow;

determining a long term RMS energy based on the flow;

determining a long term threshold based on the long term RMS energy;

determining a short term RMS energy based on the flow;

comparing the short term RMS energy with the long term threshold to determine whether such a patient is experiencing an apnea/hypopnea;

determining a short term integral of the respiratory flow;

determining a long term integral of the respiratory flow; and determines an absolute difference between the short term integral of respiratory flow and the long term integral of respiratory flow; and wherein determining whether a patient is experiencing an apnea/hypopnea event includes comparing the absolute difference to a differential threshold.

14. The method of claim 13, wherein determining the long term threshold includes multiplying the long term RMS energy by an entry threshold fraction.

15. The method of claim 13, wherein determining whether a patient is experiencing an apnea/hypopnea event includes determining whether the short term RMS energy falls below the long term threshold.

16. The method of claim 13, wherein the short term RMS energy $S_{RMS}(n)$ is determined as:

$$S_{RMS}(n) = \sqrt{\frac{1}{N_S} * \sum_{k=0}^{N_S-1} [Q(n-k)]^2},$$

where $N_S=T_S-f$, Q(n) is the patient flow, n is processing cycle, f is the sampling frequency, and $T_S$ is a period of time over which the short term RMS values is calculated.

17. The method of claim 13, wherein the long term RMS energy $L_{RMS}(n)$ is determined as:

$$L_{RMS}(n) = \sqrt{\frac{1}{N_L} * \sum_{k=0}^{N_L-1} [Q(n-k)]^2}$$

where $N_L=T_S-f$, Q(n) is the patient flow, n is processing cycle, f is the sampling frequency, and $T_L$ is a period of time over which the long term RMS values is calculated.

18. The method of claim 13, wherein the long term integral energy $L_I(n)$ is determined as:

$$L_I(n) = \sum_{k=0}^{N_L-1} Q(n-k)$$

where $N_L=T_S-f$, Q(n) is the patient flow, n is processing cycle, f is the sampling frequency, and $T_L$ is a period of time over which the long term RMS values is calculated.

19. The method of claim 13, wherein the short term integral energy $S_I(n)$ is determined as:

$$S_I(n) = \sum_{k=0}^{N_S-1} Q(n-k)$$

where $N_S=T_S-f$, Q(n) is the patient flow, n is processing cycle, f is the sampling frequency, and $T_S$ is a period of time over which the short term RMS values is calculated.

20. The method of claim 13, wherein monitoring a patient's respiratory flow comprises:

providing a conduit coupled to an airway of such a patient; and providing a flow sensor is coupled to the conduit.

21. The method of claim 13, further comprising:

providing a pressure generating system adapted to generate a flow of gas; and controlling a pressure of a flow of gas output of the pressure generating system based on whether such a patient is experiencing the apnea/hypopnea event.

22. A method of detecting an apnea/hypopnea comprising:
monitoring a patient's respiratory flow;
determining a long term RMS energy based on the flow;
determining a long term threshold based on the long term RMS energy;
determining a short term RMS energy based on the flow;
comparing the short term RMS energy with the long term threshold to determine whether such a patient is experiencing an apnea/hypopnea; and
determining whether such a patient has ceased experiencing an apnea/hypopnea event, wherein determining whether such a patient has ceased experiencing an apnea/hypopnea event comprises calculating an exit threshold and comparing the short term RMS energy with the exit threshold.

23. The method of claim 22, wherein the exit threshold is determined based on the long term threshold.

* * * * *